US012773420B2

(12) United States Patent
Mizobuchi et al.

(10) Patent No.: US 12,773,420 B2
(45) Date of Patent: Oct. 27, 2026

(54) CANCER CHEMOTHERAPY SUPPORTING AGENT, FOOD, AND DRUG

(71) Applicants: BioMedical Research Group Inc., Tokyo (JP); Gen-Ichiro Soma, Tokyo (JP)

(72) Inventors: Haruka Mizobuchi, Takamatsu (JP); Hiroyuki Inagawa, Takamatsu (JP); Chie Kohchi, Takamatsu (JP); Gen-Ichiro Soma, Tokyo (JP)

(73) Assignees: BioMedical Research Group Inc., Tokyo (JP); Gen-Ichiro Soma, Tokyo (JP)

( * ) Notice: Subject to any disclaimer, the term of this patent is extended or adjusted under 35 U.S.C. 154(b) by 991 days.

(21) Appl. No.: 17/638,919

(22) PCT Filed: Aug. 19, 2020

(86) PCT No.: PCT/JP2020/031357

§ 371 (c)(1),
(2) Date: Feb. 28, 2022

(87) PCT Pub. No.: WO2021/039554

PCT Pub. Date: Mar. 4, 2021

(65) Prior Publication Data

US 2022/0296625 A1 Sep. 22, 2022

(30) Foreign Application Priority Data

Aug. 29, 2019 (JP) ................................ 2019-156220

(51) Int. Cl.
*A61K 31/739* (2006.01)
*A23L 33/125* (2016.01)
(Continued)

(52) U.S. Cl.
CPC ........ *A61K 31/7008* (2013.01); *A23L 33/125* (2016.08); *A61K 31/505* (2013.01);
(Continued)

(58) Field of Classification Search
CPC .............. A61K 31/7008; A61K 31/505; A61K 31/739; A61K 33/243; A61K 35/741;
(Continued)

(56) References Cited

U.S. PATENT DOCUMENTS

2009/0162344 A1 6/2009 Soma et al.
2012/0251441 A1* 10/2012 Nunes .................... A61P 37/06 424/1.49
(Continued)

FOREIGN PATENT DOCUMENTS

CN 103079592 B 10/2015
JP 2012-082156 A 4/2012
(Continued)

OTHER PUBLICATIONS

Hebishima et al. (Anticancer Research., 2010, vol. 30, pp. 2033-2040) (Year: 2010).*
(Continued)

*Primary Examiner* — Andrea Olson
(74) *Attorney, Agent, or Firm* — Troutman Pepper Locke LLP

(57) ABSTRACT

In order to provide a safe food-derived ingredient that reduces side effects of a cancer chemotherapeutic agent, and particularly to provide a food, a food ingredient (supplement), and a drug that reduce lethal toxic effects of a chemotherapeutic agent, a cancer chemotherapy supporting agent, a food, and a drug according to the present invention are supporting agents for a cancer chemotherapy in which streptozotocin etc., is administered, contain a lipopolysac-
(Continued)

charide constituted of *Pantoea* bacteria LPS etc. as an active ingredient, and are orally administered.

9 Claims, 3 Drawing Sheets

(51) Int. Cl.

| | |
|---|---|
| ***A61K 31/505*** | (2006.01) |
| ***A61K 31/7008*** | (2006.01) |
| ***A61K 33/243*** | (2019.01) |
| ***A61K 35/741*** | (2015.01) |
| ***A61P 35/00*** | (2006.01) |
| ***A61P 43/00*** | (2006.01) |

(52) U.S. Cl.
CPC .......... *A61K 31/739* (2013.01); *A61K 33/243* (2019.01); *A61K 35/741* (2013.01); *A61P 35/00* (2018.01); *A61P 43/00* (2018.01)

(58) Field of Classification Search
CPC ................ A61K 31/513; A61K 31/675; A61K 31/7088; A61K 45/06; A23L 33/125; A23L 33/10; A61P 35/00; A61P 43/00
See application file for complete search history.

(56) References Cited

U.S. PATENT DOCUMENTS

| | | | |
|---|---|---|---|
| 2013/0195765 | A1 | 8/2013 | Gho et al. |
| 2014/0194287 | A1 | 7/2014 | Soma et al. |

FOREIGN PATENT DOCUMENTS

| | | | |
|---|---|---|---|
| JP | 2013-136787 A | 7/2013 |
| WO | 91/14424 A1 | 10/1991 |
| WO | 2012/173163 A1 | 12/2012 |

OTHER PUBLICATIONS

Hebishima et al. (Exp. Anim., 2011, vol. 60, pp. 101-109) (Year: 2011).*
Abdella (Iranian Journal of Cancer Prevention, 2008, vol. 4, pp. 155-165) (Year: 2008).*
Marecki et al. (Toxicology and Applied Pharmacology, 1975, vol. 31, pp. 83-92) (Year: 1975).*
Mohamed et al. (Journal of Pharmacy and Pharmacology, 2010, vol. 56, pp. 757-768) (Year: 2010).*
Oh et al. (Journal of Immunology, 2011, vol. 186, pp. 1140-1150) (Year: 2011).*
Maehara et al. (Surg Today, 2012, vol. 42, pp. 8-28) (Year: 2012).*
Ma et al. (PLOS One, 2017, vol. 12, e0171612) (Year: 2017).*
Fujihara et al. (Pharmacology & Therapeutics, 2003, vol. 100, pp. 171-194) (Year: 2003).*
Jetiyanon et al. (Biological Control, 2013, vol. 67, pp. 301-307) (Year: 2013).*
Jang et al., "Lactobacillus casei HY7213 ameliorates cyclophosphamide-induced immunosuppression in mice by activating NK, cytotoxic t cells and macrophages" Immunopharmacologyand Immunotoxicology vol. 35:3 pp. 396-402, DOI: 10.3109/08923973.2013.789055 (Year: 2013).*
Shruthi et al., "Immunomodulatory Effects of Gallic Acid against Cyclophosphamide- and Cisplatin-induced Immunosuppression in Swiss Albino Mice" Indian Journal of Pharmaceutical Sciences vol. 80(1) pp. 150-160 (Year: 2017).*
Kim et al., "Preventive effect of the Herbal Preparation, HemoHIM, on Cisplatin-induced Immune Suppression" Evidence-Based Complementary and Alternative Medicine vol. 2019 Article ID 349806, 8 pages, DOI:10.1155/2019/3494806 (Year: 2019).*
Shaw et al., "The small-molecule TNF-a inhibitor, UTL-5g, delays deaths and increases survival rates for mice treated with high doses of cisplatin" Cancer Chemother Pharmacol vol. 72 pp. 703-707, DOI: 10.1007/s00280-013-2236-4 (Year: 2013).*
Park et al., "BeneWcial eVect of metronomic chemotherapy on tumor suppression and survival in a rat model of hepatocellular carcinoma with liver cirrhosis" Cancer Chemother Pharmacol vol. 65 pp. 1029-1037, DOI:10.1007/s00280-009-1108-4 (Year: 2010).*
Santo et al., "Hydroxyl radical scavenger ameliorates cisplatin-induced nephrotoxicity by preventing oxidative stress, redox state unbalance, impairment of energetic metabolism and apoptosis in rat kidney mitochondria" Cancer Chemother Pharmacol vol. 61 pp. 145-155, DOI: 10. 1007/s00280-007-0459-y (Year: 2008).*
Kohler et al., "Influence of Streptozotocin-Induced Diabetes on Blood Pressure and on Renin Formation and Release" Naunyn-Schmiedeberg's Arch. PharmacoL vol. 313 pp. 257-261 (Year: 1980).*
1 Office Action mailed Nov. 8, 2023, issued for TW109129044.
"Numbers of Deaths, Death Rates (per 100,000 population), and Proportions of 10 Leading Causes of Death by Sex.", [online], Sep. 7, 2018, Ministry of Health, Labour and Welfare, p. 15. (discussed in the spec).
"Latest Cancer Statistics", [online], Jan. 21, 2019, National Cancer Center Japan, [retrieved on Aug. 21, 2019], pp. 1-18. (discussed in the spec).
"Cytotoxic Anticancer Agents: Controlling Side Effects by Combined Use of Preventive Drugs and Treatment Drugs", [online], Jun. 28, 2011, Akiramenai-Ganchiryo-Network, [retrieved on Aug. 21, 2019], pp. 1-5. (discussed in the spec).
"Side Effects of Chemotherapy", [online], Feb. 2, 2016, National Cancer Center Japan, [retrieved on Aug. 21, 2019], pp. 1-10. (discussed in the spec).
"Misunderstandings about Anticancer Agents and Side Effects—Can One Eat Raw Food During Anticancer Agent Treatment?—", [online], Dec. 14, 2015, The Yomiuri Shimbun, [retrieved on Aug. 21, 2019], pp. 1-10. (discussed in the spec).
"Pharmacotherapy (Chemotherapy)", [online], Jul. 22, 2019, National Cancer Center Japan, [retrieved on Aug. 21, 2019], pp. 1-16. (discussed in the spec).
N. Yoshida et al., "<Special Issue: Latest Information on Kampo Therapy.> Efficacy of Kampo Medicine for Side Effect of Anti-cancer Drug Therapy", Journal of Kyoto Prefectural University of Medicine, 2016, vol. 125, No. 2, p. 115-125. (discussed in the spec).
H. Inagawa et al., "Primed Activation of Macrophages by Oral Administration of Lipopolysaccharide Derived from Pantoea agglomerans", in vivo, 2016, 30, p. 205-211. (discussed in the spec).
Y. Kobayashi et al., "Oral administration of Pantoea agglomerans-derived lipopolysaccharide prevents metabolic dysfunction and Alzheimer's disease-related memory loss in senescence-accelerated prone 8 (SAMP8) mice fed a high-fat diet", PLoS One. Jun. 1, 2018, vol. 13, No. 6: e0198493, pp. 1-23. (discussed in the spec).
Wikipedia Japan "Streptozotocin", [retrieved on Aug. 21, 2019], Internet, pp. 1-4. (discussed in the spec).
T. Hebishima et al., "Oral Administration of Immunopotentiator from Pantoea agglomerans 1 (IP-PA1) Improves the Survival of B16 Melanoma-Inoculated Model Mice", Exp. Anim., 2011, vol. 60, No. 2, p. 101-109. (discussed in the spec).
H. Inagawa, "The Beginning of Natural Immunity through Eating, Part 5: LPS is a Functional Food Constituent", Food Style 21, 2014, vol. 18, No. 1, p. 41-43. (cited in the ISR).
Y. Chiba et al., "Antitumor Effect by Percutaneous Administration of Low Molecular Lipopolysaccharide (LPS)", Biotherapy, 1993, vol. 7, No. 3-1, p. 352-353 and English abstract. (cited in the ISR).
G. Soma, "Physiological Significance of the 'Immunity Vitamin' LPS(Lipopolysaccharide)", Bulletin of Kagawa Junior College, 2017, vol. 45, p. 333-349. (cited in the ISR).
T. Hebishima et al., "Protective Effects of the Immunopotentiator from Pantoea agglomerans 1 on Chemotherapeutic Agent-induced Macrophage Growth Inhibition", Anticancer Research, vol. 30, No. 6, 2010, p. 2033-2040. (cited in the Sep. 5, 2022 Search Report issued for EP20859608.0).
J. Dutkiewicz et al., "Pantoea agglomerans: a mysterious bacterium of evil and good. Part IV. Beneficial effects", Annals of Agricultural and Environmental Medicine, vol. 23, No. 2, 2016, p. 206-222. (cited in the Sep. 5, 2022 Search Report issued for EP20859608.0).

(56) References Cited

OTHER PUBLICATIONS

N. M. Marecki et al., "Effect of Bacterial Lipopolysaccharide, Lipid A, and Concanavalin A on Lethality of 5-Fluorouracil for Mice", Toxicology and Applied Pharmacology, vol. 31, No. 1, 1975, p. 83-92. (cited in the Sep. 5, 2022 Search Report issued for EP20859608.0).
A. Morishima et al., "Clinical Effects of Orally Administered Lipopolysaccharide Derived from Pantoea agglomerans on Malignant Tumors", Anticancer Research, vol. 36, No. 7, 2016, p. 3747-3752. (cited in the Sep. 5, 2022 Search Report issued for EP20859608.0).
Supplementary European Search Report mailed Sep. 5, 2022, issued for European Patent Application No. 20859608.0.
C. Kohchi et al., "Applications of Lipopolysaccharide Derived from Pantoea agglomerans (IP-PA1) for Health Care Based on Macrophage Network Theory", Journal of Bioscience and Bioengineering, vol. 102, No. 6, 2006, p. 485-496. (cited in the Mar. 4, 2024 Communication for EP 20 859 608.0).
M.A. Hull et al., "Activity of the non-steroidal anti-inflammatory drug indomethacin against colorectal cancer", Cancer Treatment Reviews, vol. 29, No. 4, 2003, p. 309-320. (cited in the Mar. 4, 2024 Communication for EP 20 859 608.0).
Communication from the Examining Division mailed Mar. 4, 2024, issued for EP 20 859 608.0.

* cited by examiner

CANCER CHEMOTHERAPY SUPPORTING AGENT, FOOD, AND DRUG

TECHNICAL FIELD

The present invention relates to a cancer chemotherapy supporting agent, food, and drug for reducing side effects of cancer chemotherapeutic agents.

BACKGROUND ART

<Statistics Related to Cancer>

According to statistics of the Ministry of Health, Labour and Welfare, cancer was the No. 1 cause of death in Japan in 2017 and constituted 27.9% of all causes of death (NPL 1). According to statistics compiled by the National Cancer Center Japan, the risk of contracting cancer during a lifetime is 62% for males and 47% for females, the lifetime cancer mortality risk is 25% for males and 15% for females, and cancer is the top cause of death of Japanese (NPL 2).

<Choices of Cancer Treatment>

Although treatment methods for cancer differ greatly according to site and type, generally, there are the choices of operative therapy, chemotherapy, radiation therapy, and immunotherapy, and there are also many cases where these are combined. Among these, chemotherapy (anticancer drug treatment) is the most standard therapy used and also used in combination with other therapies.

Cancer Chemotherapeutic Agents Include

- antimetabolites (substances that inhibit use of metabolites that are produced and exhibit DNA synthesis inhibitory action on dividing cells; drug examples: 5-fluorouracil (5-FU), cytarabine, cladribine, etc.),
- alkylating agents (exhibit cytostatic action by alkylating DNA and crosslinking guanine bases of the double chain to each other; drug examples: cyclophosphamide, melphalan, ifosfamide, busulfan, streptozotocin, etc.),
- microtubule affecting agents (exhibit polymerization inhibiting action by binding to tubulin that forms microtubules; drug examples: paclitaxel, docetaxel, vincristine, vinblastine, etc.),
- topoisomerase inhibiting agents (exhibit action of inhibiting DNA rebinding by acting on topoisomerase that synthesizes the DNA of cancer cells; drug examples: irinotecan, etoposide, etc.),
- anticancer antibacterial agents (action mechanism differs according to drug; drug examples: doxorubicin, bleomycin, mitomycin C, etc.),
- platinating agents (exhibit DNA insertion and polymerase inhibiting actions; drug examples: cisplatin, epirubicin, carboplatin, etc.) (NPL 3). For all of these, the grounds of selectivity are deemed to be based on cancer cells being higher in proliferative ability than normal cells.

<Side Effects of Chemotherapeutic Agents>

However, with chemotherapeutic agents, even normal cells that are high in mitotic rate such as blood (bone marrow) cells, mucosal tissue cells, hair root cells, etc., receive inhibitory actions like cancer cells. Consequently, increased susceptibility to infection, anemia, bleeding, nausea, stomatitis, diarrhea, change in taste sensation, hair loss, skin disorder, change in nails, death, and other symptoms occur as side effects (NPL 4). Examples of chemotherapeutic agents with which the frequency of side effects is high and nausea occurs readily are AC therapy (doxorubicin+cyclophosphamide), EC therapy (epirubicin+cyclophosphamide), cyclophosphamide, cisplatin, streptozocin, dacarbazine, etc., and these have an emesis incidence exceeding 90%. Also, actinomycin D, azacytidine, amrubicin, idarubicin, ifosfamide, irinotecan, enocitabine, epirubicin, oxaliplatin, carboplatin, clofarabine, arsenic trioxide, cyclophosphamide, cytarabine, daunorubicin, temozolomide, doxorubicin, nedaplatin, pirarubicin, busulfan, bendamustine, miriplatin, methotrexate, melphalan, etc., are also deemed to have an emesis incidence of 30 to 90%. As antiemetics for emesis, aprepitant, serotonin receptor antagonists, and dexamethasone are mainly used. Further, late onset diarrhea associated with intestinal mucosal disorder occurs frequently as a side effect of anticancer agents. Irinotecan, methotrexate, docetaxel, 5-FU, capecitabine, cytarabine, doxorubicin, etc., are known as cancer chemotherapeutic agents with which diarrhea is frequently observed. With adriamycin, epirubicin, docetaxel, and paclitaxel, the hair of the head falls off in most patients. Due to these side effects, many patients give up on chemotherapy in the middle of treatment. Also, infection during leucopenia is deemed to be the most frequent cause of death as side effect of anticancer agents (NPL 5).

<Conventional Arts for Reducing Side Effects>

Side effects occur in most chemotherapeutic agent treatments and in some cases, the side effect emerges more strongly than the effect (NPL 3). Such a background gave rise in recent years to the concept of symptomatic therapy (supportive therapy) for relieving symptoms with respect to symptoms accompanying cancer and side effects due to treatment. Specifically, drugs for suppressing nausea (serotonin blockers and dexamethasone), antidiarrheics and intestinal regulators for diarrhea, purgatives for constipation, anti-inflammatory agents and analgesics for stomatitis, antibiotics for infection, blood transfusion for supplementing anemia, vitamin preparations for numbness caused by microtubule affecting agents etc., are used (NPL 6). However, although there are patients with whom alleviation of symptoms to some degree is seen, sufficient effects are not obtained in many cases and it cannot yet be said that an effective supportive therapy is established (NPL 7).

Current supporting therapies are symptomatic treatment agents administered to patients after symptoms are expressed as side effects due to chemotherapeutic agents in accordance with the symptoms. If side effects of chemotherapeutic agents can be reduced with foods, this would be a safe and excellent supportive therapy. Although Kampo medicines that reduce side effects of cancer chemotherapeutic agents have been reported up to now (NPL 7), safe foods or food ingredients that patients can ingest freely have not been established. There has thus been a demand for safe foods, food ingredients (supplements), and drugs that can safely prevent side effects of chemotherapeutic agents.

CITATION LIST

Non Patent Literature

[NPL 1] "Numbers of Deaths, Death Rates (per 100,000 population), and Proportions of 10 Leading Causes of Death by Sex.", [online], Sep. 7, 2018, Ministry of Health, Labour and Welfare, [retrieved on Aug. 21, 2019], Internet, <https://www.mhlw.go.jp/toukei/saikin/hw/jinkou/kakutei17/dl/10_h6.pdf>

[NPL 2] "Latest Cancer Statistics", [online], Jan. 21, 2019, National Cancer Center Japan, [retrieved on Aug. 21, 2019], Internet, <https://ganjoho.jp/reg_stat/statistics/stat/summary.html>

[NPL 3] "Cytotoxic Anticancer Agents: Controlling Side Effects by Combined Use of Preventive Drugs and Treatment Drugs", [online], Jun. 28, 2011, AKIRAMENAI-GANCHIRYO-NETWORK, [retrieved on Aug. 21, 2019], Internet, <https://www.akiramenai-gan.com/medical contents/disease/1927/2/>

[NPL 4] "Side Effects of Chemotherapy", [online], Feb. 2, 2016, National Cancer Center Japan, [retrieved on Aug. 21, 2019], Internet, <https://ganjoho.jp/child/dia_tre/treatment/side_effect01.html>

[NPL 5] "Misunderstandings about Anticancer Agents and Side Effects—Can One Eat Raw Food During Anticancer Agent Treatment?—", [online], Dec. 14, 2015, The Yomiuri Shimbun, [retrieved on Aug. 21, 2019], Internet, <https://yomidr.yomiuri.co.jp/article/20151214-OYTEW55388/>

[NPL 6] "Pharmacotherapy (Chemotherapy)", [online], Jul. 22, 2019, National Cancer Center Japan, [retrieved on Aug. 21, 2019], Internet, <https://ganjoho.jp/public/dia_tre/treatment/drug_therapy.html>

[NPL 7] Naohisa Yoshida and 2 others, "<Special Issue: Latest Information on Kampo Therapy.> Efficacy of Kampo Medicine for Side Effect of Anti-cancer Drug Therapy", Journal of Kyoto Prefectural University of Medicine, 2016, 125(2), pp. 115-125.

[NPL 8] H. Inagawa et al., "Primed Activation of Macrophages by Oral Administration of Lipopolysaccharide Derived from *Pantoea agglomerans*", in vivo, 2016, 30, pp. 205-211.

[NPL 9] Y. Kobayashi et al., "Oral administration of *Pantoea agglomerans*-derived lipopolysaccharide prevents metabolic dysfunction and Alzheimer's disease-related memory loss in senescence-accelerated prone 8 (SAMP8) mice fed a high-fat diet", PLoS ONE. 2018, 13(6): e0198493.

[NPL 10] Wikipedia Japan "Streptozotocin", [retrieved on Aug. 21, 2019], Internet

[NPL 11] T. Hebishima et al., "Oral Administration of Immunopotentiator from *Pantoea agglomerans* 1 (IP-PA1) Improves the Survival of B16 Melanoma-Inoculated Model Mice", Exp. Anim., 2011, 60(2), pp. 101-109.

SUMMARY OF INVENTION

Technical Problem

In view of the current circumstances described above, an object of the present invention is to provide a safe food-derived ingredient that reduces side effects of a cancer chemotherapeutic agent. In particular, an object is to provide a food, a food ingredient (supplement), and a drug that reduce lethal toxic effects of a chemotherapeutic agent.

Solution to Problem

A cancer chemotherapy supporting agent, food, or drug according to the present invention is a cancer chemotherapy supporting agent, food, or drug for reducing side effects of cancer chemotherapy and increasing the administration amounts of chemotherapeutic agents that is characterized in containing a lipopolysaccharide as an active ingredient.

Also, it is characterized in that the cancer chemotherapy is that in which an alkylating agent is administered.

Also, it is characterized in that the alkylating agent is streptozotocin or cyclophosphamide.

Also, it is characterized in that the cancer chemotherapy is that in which a platinating agent is administered.

Also, it is characterized in that the platinating agent is cisplatin.

Also, it is characterized in that the cancer chemotherapy is that in which an antimetabolite is administered.

Also, it is characterized in that the antimetabolite is 5-fluorouracil.

Also, it is characterized in that the supporting agent is orally administered.

Also, it is characterized in that the lipopolysaccharide is derived from a bacterium belonging to family Enterobacteriaceae.

Also, it is characterized in that the lipopolysaccharide is derived from a bacterium belonging to genus *Pantoea* or derived from a bacterium belonging to genus *Enterobacter.*

To achieve the above object, the present inventors found from research results up to now that by allowing oral ingestion of a lipopolysaccharide (LPS) derived from gram negative bacteria and having a function of increasing healing power, a novel supportive therapy based on ingestion of a safe food, food ingredient (supplement), or drug that reduces side effects of a chemotherapeutic agent can be constructed.

A living body, upon receiving cellular damage or tissue damage, is cured by induction of cytokines, involved in cellular proliferation and tissue repair from phagocytes (macrophages etc.) and epithelial cells, such as fibroblast growth factors (FGF) vascular endothelial growth factor (VEGF), keratinocyte growth factor (KGF), platelet-derived growth factors (PDGF), tumor necrosis factor (TNF), etc., and interleukin-6 (IL-6) etc. LPSs are also known to induce these cytokines by binding to toll-like receptor 4 (TLR4) expressed on phagocytes and epithelial cells in cell assays or by injection administration. However, LPS oral administration differs completely in effect from cell stimulation assays and an effect of inducing the above cytokines that promote recovery from damage of a living body by oral administration of LPSs was not known (NPL 8).

When the influence of LPS oral administration on glial cell line-derived neurotrophic factor (GNDF), which is known to exhibit cell death inhibition, was examined, it was found that gene expression of glial cell line-derived neurotrophic factor (GNDF) is increased significantly by LPS oral administration. This suggests the possibility that LPS oral administration exhibits an action of preventing cellular damage or tissue damage of a living body that is caused by one reason or another.

A cancer chemotherapeutic agent inflicts damage on normal dividing cells and there is thus a possibility that damage is occurring even in tissue with which a side effect is not apparent. In tissue in which cellular damage occurs concentratedly, this is observed as a symptom of side effect in the tissue. The most serious side effect is death of an individual. It is thus considered that the benefits of oral ingestion of LPS as a supportive therapy can be evaluated using an animal model in which death of an individual induced by cancer chemotherapy is prevented. With the present invention, death prevention effect by oral administration of LPS was clarified using models of death by cancer chemotherapeutic agents in mice.

The LPSs that are used as supportive therapy agents are substances that are present in the environment and are substances that are not only ingested to some degree even in daily life but are also being blended in foods and cosmetics. Through oral ingestion, LPSs increase functionality of intraperitoneal and intracerebral phagocytes (macrophages) (NPLs 8 and 9). Also, activated phagocytes have a function of repairing tissue damage inside a living body. Although as LPSs, LPSs derived from bacteria belonging to genus *Pantoea*, bacteria belonging to genus *Enterobacter*, bacteria belonging to genus *Xanthomonas*, bacteria belonging to family Acetobacteraceae, and bacteria belonging to genus *Zymomonas* that are plant symbiotic bacteria with history of use in foods can be cited, as long as an LPS is used, it is not necessary to specify the bacterial strain.

As cancer chemotherapeutic agents, generally used antimetabolites (substances that inhibit use of metabolites that are produced and inhibit DNA production in dividing cells; 5-fluorouracil (5-FU), cytarabine, cladribine, etc.), alkylating agents (that stop cell division by alkylating DNA and crosslinking guanine bases of the double chain to each other; cyclophosphamide, melphalan, ifosfamide, busulfan, streptozotocin, etc.), microtubule affecting agents (that bind to tubulin, which forms microtubules, to inhibit polymerization; paclitaxel, docetaxel, vincristine, vinblastine, etc.), topoisomerase inhibiting agents (that inhibit rebinding of DNA by acting on topoisomerase that synthesizes the DNA of cancer cells; irinotecan, etoposide, etc.), anticancer antibacterial agents (action mechanism differs according to drug; doxorubicin, bleomycin, mitomycin C, etc.), platinating agents (that inhibit DNA insertion and polymerases; cisplatin, epirubicin, carboplatin, etc.) and the like that exhibit cytotoxic action are applicable.

Advantageous Effects of Invention

By side effects (increased susceptibility to infection, anemia, bleeding, nausea, stomatitis, diarrhea, change in taste sensation, hair loss, skin disorder, change in nails, death, etc.) due to cancer chemotherapeutic agents being reduced by oral ingestion of the LPS of the present invention, patients being treated for cancer will become able to lead an ordinary life without degradation of quality of life (QOL). Also, by making it possible to increase the administration amounts of chemotherapeutic agents, increase in cancer curing effect can also be anticipated.

LPSs are food ingredients and since there are no side effects at all even when ingested by a healthy individual, foods and food ingredients (supplements) can be ingested by anybody. The advantages that use in combination with various choices of cancer treatment is possible and that continued use before, during, and even after treatment does not present a problem are thus provided.

DESCRIPTION OF EMBODIMENTS

Examples of the present invention shall be described.

Example 1

Reduction of toxic effects of the chemotherapeutic agent streptozotocin by LPS oral administration (1) Method 1) Reagents LPS (LPSp) derived from *Pantoea agglomerans* belonging to genus *Pantoea* of family Enterobacteriaceae (mac0001 of Macrophi Inc.)

Streptozotocin (STZ) (SAJ-S0130 of Sigma-Aldrich)

2) Mice and Husbandry

Six-week-old male C57BL mice were used. Husbandry of the mice was carried out in a temperature and humidity controlled animal facility under environmental conditions of ad libitum food and water, and 12 hr light/12 hr dark. As food, the D12450B diet of Research Diets, Inc. was provided. After 1 week of preliminary rearing, the mice were divided into 3 groups of 6 mice each.

3) Test

PBS administration group (PBS i.p.): 0.5 mL of phosphate buffer saline (PBS) were injected into the peritoneal cavity of each mouse.

STZ administration group (STZ i.p.): An STZ solution (250 mg/kg) was injected into the peritoneal cavity of each mouse.

STZ+LPS administration group (STZ i.p.+LPS): The STZ solution (250 mg/kg) was injected into the peritoneal cavity of each mouse and LPSp was mixed in drinking water such as to be of 100 μg/kg body weight/day and allowed to be ingested ad libitum.

(2) Results

Figure 1:
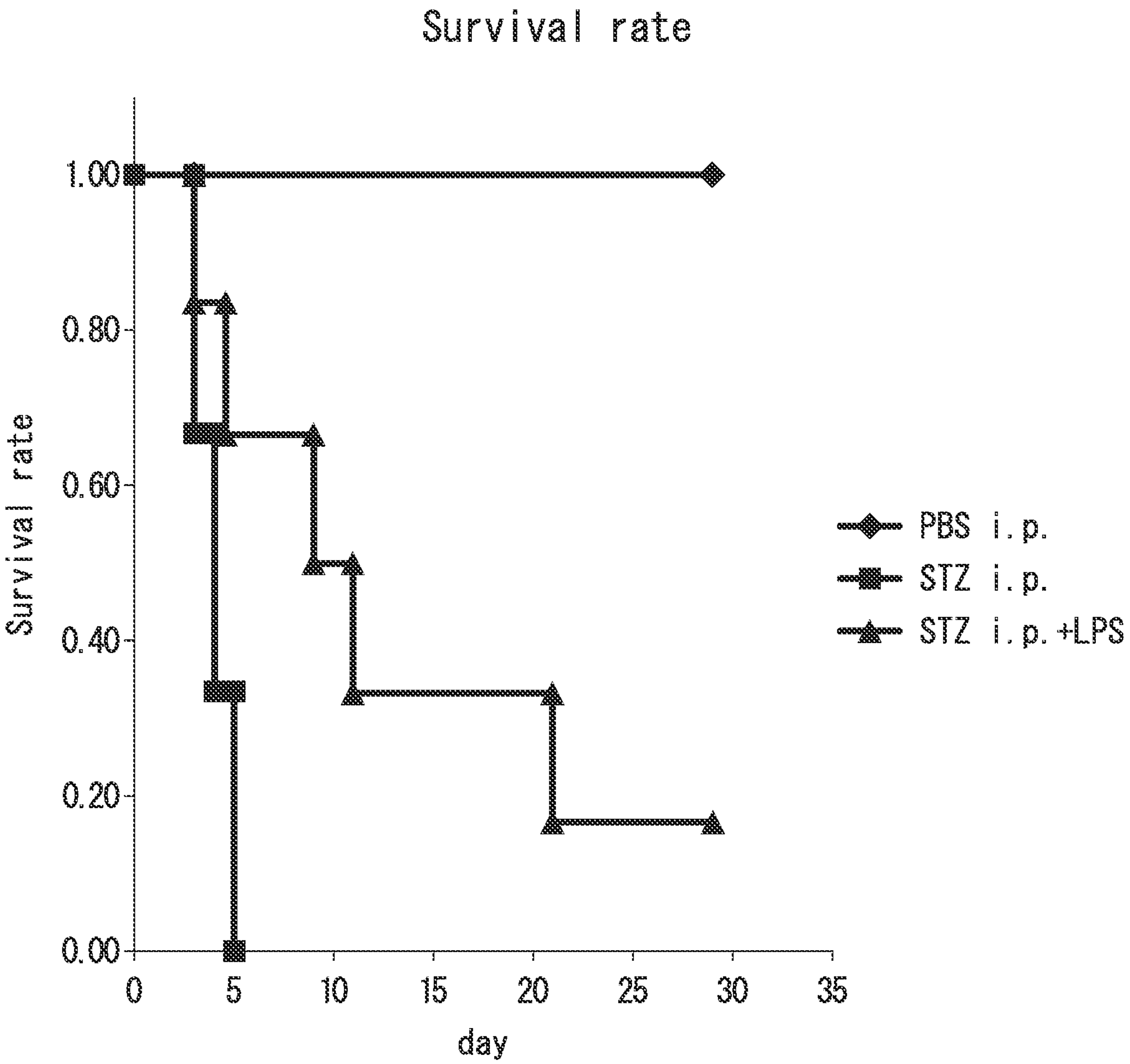
FIG. 1 is a diagram showing results of an experiment of Example 1 of the present invention.

The chemotherapeutic agent STZ is known to produce various toxic effects (nephropathy, myelosuppression (leukocytopenia, lymphocytopenia, neutropenia, thrombocytopenia, anemia, etc.), impaired glucose tolerance (hyperglycemia, increased blood insulin, increased insulin C peptide, and positive urine glucose), hepatopathy, etc. (NPL 10). On measuring the survival rate in the present test, it was found that on the 5th day, although there were no dead mice in the PBS administration group (PBS i.p.), 6 out of 6 mice died in the STZ administration group (STZ i.p.), and 4 out of 6 mice survived in the STZ+LPS administration group (STZ i.p.+LPS). On the 29th day, 1 out of 6 mice survived in the STZ+LPS administration group (Kaplan-Meier test: $P<0.05$). From the above, it was shown that LPSp administration has an effect of reducing the toxic effects of STZ (FIG. 1, Table 1).

TABLE 1

| Survival rate (%) | | | |
|---|---|---|---|
| day | PBS i.p. | STZ i.p. | STZ i.p. + LPS |
| 3 | 100 | 66.7 | 83.3 |
| 4 | 100 | 33.3 | 83.3 |
| 4.5 | 100 | 33.3 | 66.7 |
| 5 | 100 | 0.0 | 66.7 |
| 9 | 100 | 0.0 | 50.0 |
| 11 | 100 | 0.0 | 33.3 |
| 21 | 100 | 0.0 | 16.7 |
| 29 | 100 | 0.0 | 16.7 |

Although prevention of side effects of a cancer chemotherapeutic agent by LPS oral administration was examined with *Pantoea agglomerans*-derived LPS (LPSp), this effect is obtained with all LPSs that can induce a protective action to tissue damage by activation of macrophages and is thus not limited to LPS derived from bacteria belonging to genus *Pantoea*.

Example 2

Reduction of toxic effects of the platinating agent cisplatin by LPS oral administration (1) Method 1) Reagents

*Pantoea agglomerans*-derived LPS (LPSp) (mac0001 of Macrophi Inc.)

Cisplatin (CDDP) (033-20091 of FUJIFILM Wako Pure Chemical Corporation)

2) Mice and Husbandry

Four-week-old male ICR mice were used. Husbandry of the mice was carried out in a temperature and humidity controlled animal facility under environmental conditions of ad libitum food and water, and 12 hr light/12 hr dark. As food, CE-12 of CLEA Japan, Inc. was provided. After measuring the body weights at the time of delivery, the mice were divided into 3 groups of 6 mice each.

3) Test

Physiological saline administration group (saline i.p.): 0.5 mL of physiological saline were injected into the peritoneal cavity of each mouse.

Cisplatin administration group (CDDP i.p.): A cisplatin solution (17.4 mg/kg) was injected into the peritoneal cavity of each mouse.

Cisplatin+LPS administration group (CDDP i.p.+LPS): The cisplatin solution (17.4 mg/kg) was injected into the peritoneal cavity of each mouse and LPSp was mixed in drinking water such as to be of 1 mg/kg body weight/day and allowed to be ingested ad libitum.

(2) Results

Figure 2:
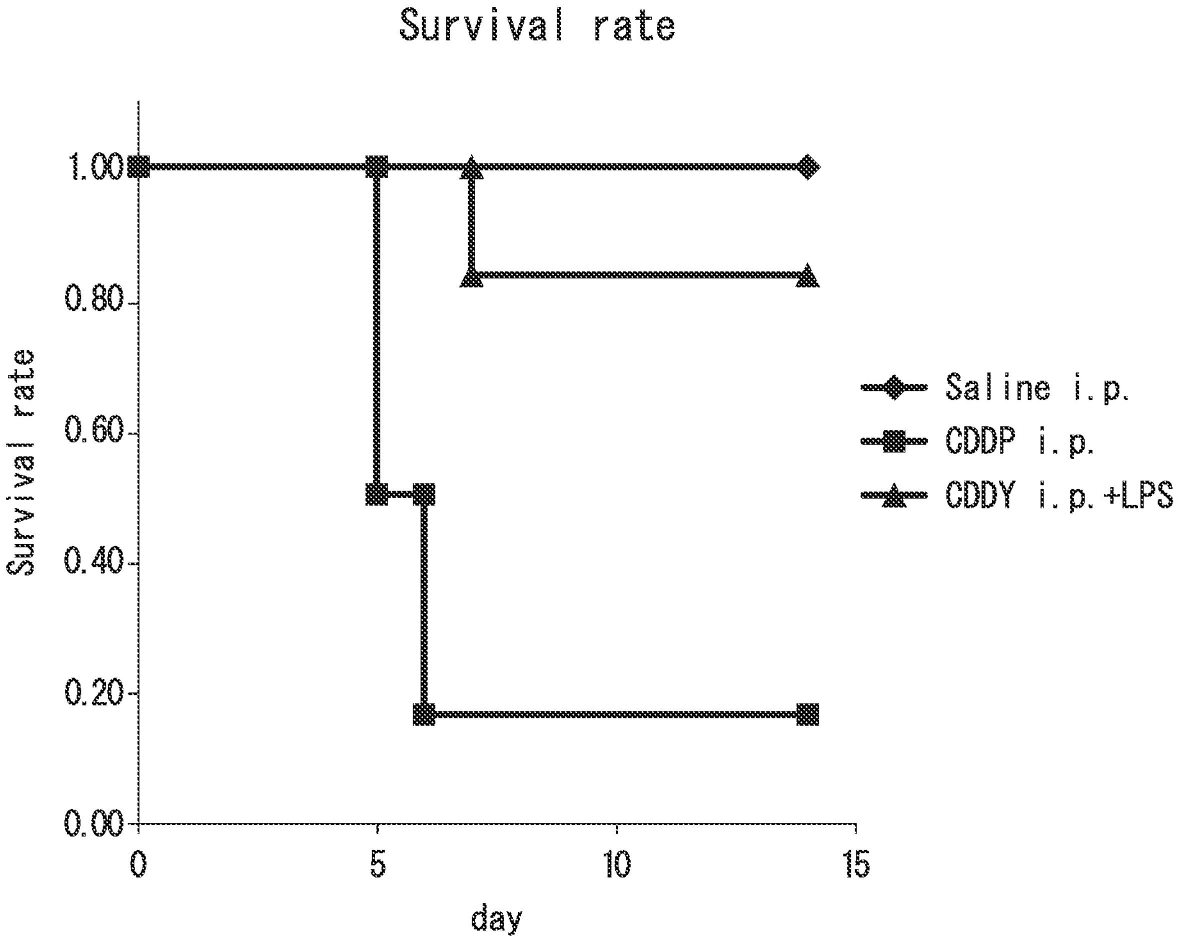
FIG. 2 is a diagram showing results of an experiment of Example 2 of the present invention.

The chemotherapeutic agent cisplatin is known for various side effects (acute renal failure, abnormal BUN value, hematuria, etc.). On measuring the survival rate in the present test, it was found that by the 6th day from anticancer agent administration, although there were no dead mice in the physiological saline administration group (saline i.p.) and the cisplatin+LPS administration group (CDDP i.p.+LPS), 5 out of 6 mice died in the cisplatin administration group (CDDP i.p.). On the 14th day, 1 out of 6 mice survived in the cisplatin administration group and 5 out of 6 mice survived in the cisplatin+LPS administration group (Kaplan-Meier test: P<0.05). From the above, it was shown that LPSp administration has an effect of reducing the toxic effects of cisplatin (FIG. 2, Table 2).

TABLE 2

| | Survival rate (%) | | |
|---|---|---|---|
| day | Saline i.p. | CDDP i.p. | CDDP i.p. + LPS |
| 5 | 100 | 50 | 100 |
| 6 | 100 | 16.7 | 100 |
| 7 | 100 | 16.7 | 83.3 |
| 14 | 100 | 16.7 | 83.3 |

Example 3

Reduction of toxic effects of the alkylating agent cyclophosphamide by LPS oral administration (1) Method 1) Reagents

*Pantoea agglomerans*-derived LPS (LPSp) (mac0001 of Macrophi Inc.)

Cyclophosphamide (CY) (030-12953 of FUJIFILM Wako Pure Chemical Corporation)

2) Mice and Husbandry

Four-week-old male ICR mice were used. Husbandry of the mice was carried out in a temperature and humidity controlled animal facility under environmental conditions of ad libitum food and water, and 12 hr light/12 hr dark. As food, CE-12 of CLEA Japan, Inc. was provided. After measuring the body weights at the time of delivery, the mice were divided into 3 groups of 6 mice each.

3) Test

Physiological saline administration group (saline i.p.): 0.5 mL of physiological saline were injected into the peritoneal cavity of each mouse.

Cyclophosphamide administration group (CY i.p.): A cyclophosphamide solution (440 mg/kg) was injected into the peritoneal cavity of each mouse.

Cyclophosphamide+LPS administration group (CY i.p.+LPS): The cyclophosphamide solution (440 mg/kg) was injected into the peritoneal cavity of each mouse and LPSp was mixed in drinking water such as to be of 1 mg/kg body weight/day and allowed to be ingested ad libitum.

(2) Results

The chemotherapeutic agent cyclophosphamide is known for various side effects (leukocytopenia, vomiting, hair loss, etc.). On measuring the body weights in the present test, significant weight loss in comparison to the physiological saline administration group (saline i.p.) was seen with the cyclophosphamide administration group (CY i.p.) and the cyclophosphamide+LPS administration group (CY i.p.+LPS) on the 3rd day from anticancer agent administration. On the 11th day and 13th day from administration, although significant weight loss in comparison to the physiological saline administration group was seen with the cyclophosphamide administration group (Tukey's multiple comparison test: P<0.05), a significant difference was not seen with the cyclophosphamide+LPS administration group (Table 3). From the above, it was shown that LPSp administration has an effect of suppressing weight loss due to cyclophosphamide.

TABLE 3

| | Mice body weights after anticancer agent administration (relative value in % with body weights for saline i.p. being 100) | | | |
|---|---|---|---|---|
| | 0 day | 3 day | 11 day | 13 day |
| Saline i.p. | 100 ± 2.9 | 100 ± 3.3 | 100 ± 3.0 | 100 ± 2.4 |
| CY i.p. | 98.6 ± 3.0 | 80.3 ± 4.4 ** | 85.1 ± 3.2 * | 84.8 ± 3.9 * |
| CY i.p. + LPS | 100 ± 8.9 | 82.9 ± 13.3 ** | 91.8 ± 13.1 | 92.3 ± 13.5 |

* P < 0.05;
** P < 0.01 (with respect to saline i.p.)

Example 4

Reduction of Toxic Effects of the Antimetabolite 5-fluorouracil by LPS Oral Administration (1) Method 1) Reagents

*Pantoea agglomerans*-derived LPS (LPSp) (mac0001 of Macrophi Inc.)

5-fluorouracil (5-FU) (068-01401 of FUJIFILM Wako Pure Chemical Corporation)

2) Mice and Husbandry

Four-week-old male ICR mice were used. Husbandry of the mice was carried out in a temperature and humidity controlled animal facility under environmental conditions of ad libitum food and water, and 12 hr light/12 hr dark. As food, CE-12 of CLEA Japan, Inc. was provided. After measuring the body weights at the time of delivery, the mice were divided into 3 groups of 6 mice each.

3) Test

Physiological saline administration group (saline i.p.): 0.5 mL of physiological saline were injected into the peritoneal cavity of each mouse.

5-fluorouracil administration group (5-FU i.p.): A 5-fluorouracil solution (360 mg/kg) was injected into the peritoneal cavity of each mouse.

5-fluorouracil+LPS administration group (5-FU i.p.+LPS): The 5-fluorouracil solution (360 mg/kg) was injected into the peritoneal cavity of each mouse and LPSp was mixed in drinking water such as to be of 1 mg/kg body weight/day and allowed to be ingested ad libitum.

(2) Results

The chemotherapeutic agent 5-fluorouracil is known for various side effects (leukocytopenia, diarrhea, melena, dysorexia, etc.). On measuring the body weights in the present test, on the 3rd day from anticancer agent administration, whereas a comparison of the physiological saline administration group (saline i.p.) and the 5-fluorouracil administration group (5-FU i.p.) showed a significant weight loss in the 5-fluorouracil administration group (5-FU i.p.) (Tukey's multiple comparison test: P<0.05), a significant difference was not seen between the physiological saline administration group (saline i.p.) and the 5-fluorouracil+LPS administration group (5-FU i.p.+LPS).

Also, on the 6th day, a comparison of the 5-fluorouracil administration group (5-FU i.p.) and the 5-fluorouracil+LPS administration group (5-FU i.p.+LPS) showed the 5-fluorouracil administration group (5-FU i.p.) to be significantly low (Tukey's multiple comparison test: P<0.05). From the above, it was shown that LPSp administration has an effect of reducing the toxic effects of 5-fluorouracil (Table 4).

TABLE 4

| Mice body weights after anticancer agent administration (relative value in % with body weights for saline i.p. being 100) | | | |
|---|---|---|---|
| | 0 day | 3 day | 6 day |
| Saline i.p. | 100 ± 5.7 | 100 ± 6.2 | 100 ± 10.7 |
| 5-FU i.p. | 102.0 ± 2.4 | 91.8 ± 4.1 * | 94.5 ± 2.6 |
| 5-FU i.p. + LPS | 106.1 ± 5.7 | 98.1 ± 5.6 | 106.4 ± 5.9 ** |

* P < 0.05 (with respect to saline i.p.)
** P < 0.05 (with respect to 5-FU i.p.)

Example 5

Reduction of toxic effects of the alkylating agent streptozotocin by LPS oral administration (1) Method 1) Reagents LPS (LPSea) derived from *Enterobacter asburiae* belonging to genus *Enterobacter* of family Enterobacteriaceae (Macrophi Inc.)

Streptozotocin (STZ) (SAJ-S0130 of Sigma-Aldrich)

2) Mice and Husbandry

Six-week-old male C57BL mice were used. Husbandry of the mice was carried out in a temperature and humidity controlled animal facility under environmental conditions of ad libitum food and water, and 12 hr light/12 hr dark. As food, the D12450B diet of Research Diets, Inc. was provided. After measuring the body weights at the time of delivery, the mice were divided into 3 groups of 6 mice each.

3) Test

Physiological saline administration group (saline i.p.): 0.5 mL of physiological saline were injected into the peritoneal cavity of each mouse.

STZ administration group (STZ i.p.): An STZ solution (313 mg/kg) was injected into the peritoneal cavity of each mouse.

STZ+LPS administration group (STZ i.p.+LPSea): The cisplatin solution (313 mg/kg) was injected into the peritoneal cavity of each mouse and LPSea was mixed in drinking water such as to be of 1 mg/kg body weight/day and allowed to be ingested ad libitum.

(2) Results

Figure 3:
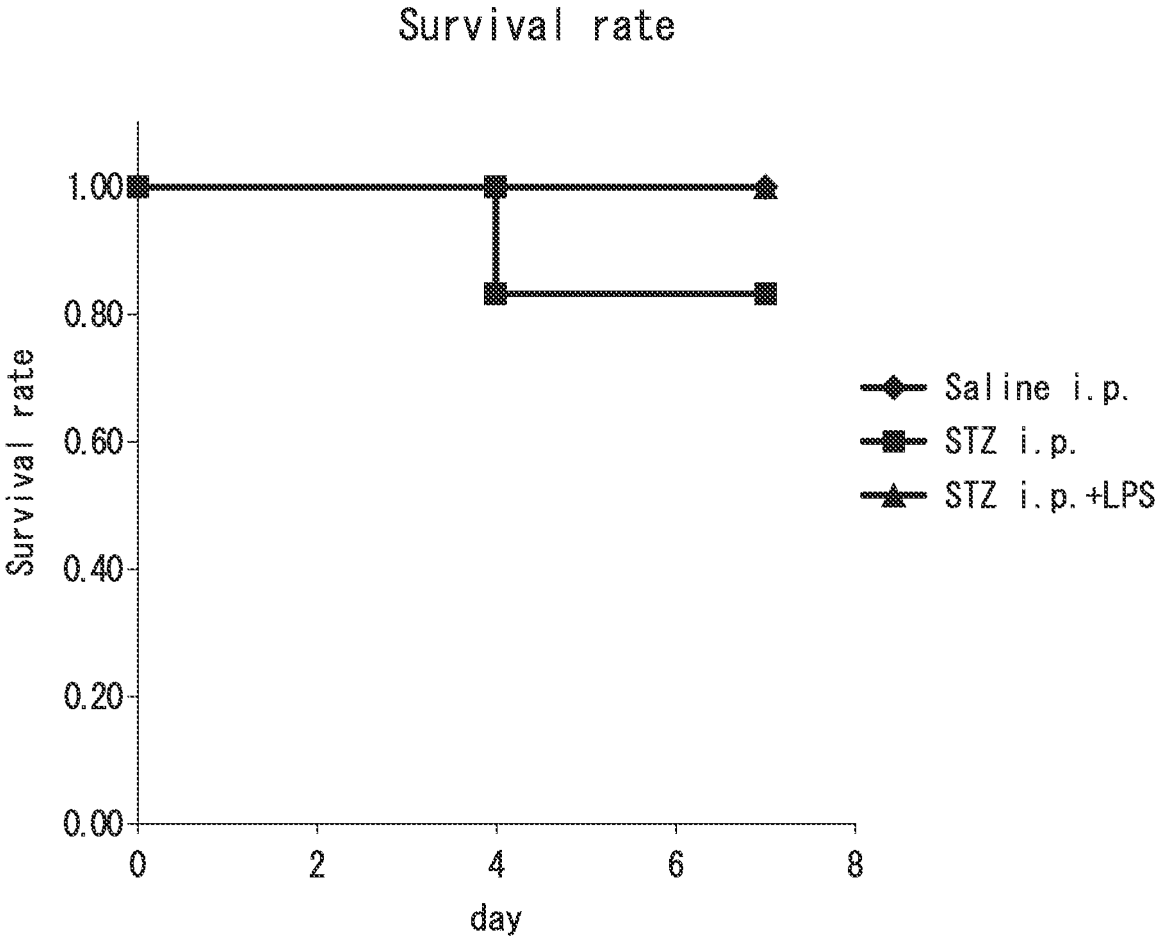
FIG. 3 is a diagram showing results of an experiment of Example 5 of the present invention.

On measuring the survival rate in the present test, it was found that by the 4th day from anticancer agent administration, although there were no dead mice in the physiological saline administration group (saline i.p.) and the STZ+LPS administration group (STZ i.p.+LPSea), 1 out of 6 mice died in the STZ administration group (STZ i.p.). From the above, it was shown that LPSea administration has an effect of reducing the toxic effects of streptozotocin (FIG. 3, Table 5).

TABLE 5

| Survival rate (%) | | | |
|---|---|---|---|
| day | Saline i.p. | STZ i.p. | STZ i.p. + LPSea |
| 3 | 100 | 100 | 100 |
| 4 | 100 | 83.33 | 100 |
| 8 | 100 | 83.33 | 100 |

In NPL 11, it is stated that in comparison to using the anticancer agent doxorubicin alone, there is an increase in IFN-γ etc., that contribute to cancer treatment when IP-PA1, which is a *Pantoea agglomerans*-derived LPS, is used in combination, that is, cancer treatment effects are improved by combined use of *Pantoea agglomerans*-derived LPS with doxorubicin.

On the other hand, the present invention suppresses the side effects of anticancer agents and can therefore improve the quality of medical treatment life to provide opportunities for treatment by anticancer agents to a larger number of patients and further enables larger amounts of anticancer agents to be administered to patients.

The disclosure of Japanese Patent Application No. 2019-156220 filed on Aug. 29, 2019 that includes a description, claims, and drawings is incorporated herein by reference in its entirety.

All publications, patents, and patent applications cited in this Description are incorporated herein by reference in their entirety.

The invention claimed is:

1. A method comprising:

utilizing a substance with lipopolysaccharide as an active ingredient as an adjuvant in a cancer treatment regimen, the treatment regimen comprising:

orally administering to a living body the adjuvant at a dose of about 0.1 mg/kg to about 1 mg/kg body weight of the living body; and administering a dose of a chemotherapeutic agent in an amount increased above an amount of the chemotherapeutic agent administered had the adjuvant had not been administered to the living body;

wherein administration of the adjuvant causes a reduction of a side effect of the chemotherapeutic agent allowing the chemotherapeutic agent to be administered at the increased amount thereby increasing an efficacy of the chemotherapeutic agent, wherein the chemotherapeutic agent includes an alkylating agent, and the side effect is induced by the alkylating agent, wherein the alkylating agent is cyclophosphamide and wherein the side effect is weight loss induced by the cyclophosphamide and wherein the dose of the cyclophosphamide is about 400 mg/kg body weight of the living body or more.

2. The method according to claim 1, wherein the lipopolysaccharide is derived from a bacterium belonging to family Enterobacteriaceae.

3. The method according to claim 1, wherein the lipopolysaccharide is derived from a bacterium belonging to genus *Pantoea* or derived from a bacterium belonging to genus *Enterobacter*.

4. The method according to claim 3, wherein the lipopolysaccharide is derived from *Pantoea agglomerans*.

5. The method according to claim 3, wherein the lipopolysaccharide is derived from *Enterobacter asburiae*.

6. The method according to claim 1, wherein the substance is a member selected from the group consisting of supplement, food and drug.

7. A method comprising:

utilizing a substance with lipopolysaccharide as an active ingredient as an adjuvant in a cancer treatment regimen, the treatment regimen comprising:

orally administering to a living body the adjuvant at a dose of about 1 mg/kg body weight of the living body;

administering a dose of a chemotherapeutic agent in an amount increased above an amount of the chemotherapeutic agent administered had the adjuvant had not been administered to the living body;

wherein administration of the adjuvant causes a reduction of a side effect of the chemotherapeutic agent allowing the chemotherapeutic agent to be administered at the increased amount thereby increasing an efficacy of the chemotherapeutic agent, wherein the chemotherapeutic agent includes a platinating agent, wherein the platinating agent is cisplatin, and wherein the side effect is decreased survival rate induced by the cisplatin, wherein the dose of the cisplatin is about 17 mg/kg body weight of the living body.

8. A method comprising:

utilizing a substance with lipopolysaccharide as an active ingredient as an adjuvant in a cancer treatment regimen, the treatment regimen comprising:

orally administering to a living body the adjuvant at a dose of about 1 mg/kg body weight of the living body;

administering a dose of a chemotherapeutic agent in an amount increased above an amount of the chemotherapeutic agent administered had the adjuvant had not been administered to the living body;

wherein administration of the adjuvant causes a reduction of a side effect of the chemotherapeutic agents allowing the chemotherapeutic agent to be administered at the increased amount thereby increasing an efficacy of the chemotherapeutic agent, wherein the chemotherapeutic agent includes an antimetabolite, wherein the antimetabolite is 5-fluorouracil and wherein the side effect is weight loss induced by 5-fluorouracil, wherein the dose of the 5-fluorouracil is about 300 mg/kg body weight of the living body.

9. A method comprising:

utilizing a substance with lipopolysaccharide as an active ingredient as an adjuvant in a cancer treatment regimen, the treatment regimen comprising:

orally administering to a living body the adjuvant at a dose of about 0.1 mg/kg to about 1 mg/kg body weight of the living body; and administering a dose of a chemotherapeutic agent in an amount increased above an amount of the chemotherapeutic agent administered had the adjuvant had not been administered to the living body;

wherein administration of the adjuvant causes a reduction of a side effect of the chemotherapeutic agent allowing the chemotherapeutic agent to be administered at the increased amount thereby increasing an efficacy of the chemotherapeutic agent, wherein the chemotherapeutic agent includes an alkylating agent, and the side effect is induced by the alkylating agent, wherein the alkylating agent is streptozotocin and wherein the side effect is decreased survival rate induced by the streptozotocin and wherein the dose of streptozotocin is about 250 mg/kg to about 313 mg/kg body weight of the living body.

* * * * *